(12) United States Patent
Gomez

(10) Patent No.: US 7,736,605 B1
(45) Date of Patent: Jun. 15, 2010

(54) INCENSE TIMER

(76) Inventor: Ralph Gregory Gomez, 131 Southern Heights Blvd., San Rafael, CA (US) 94901

( * ) Notice: Subject to any disclaimer, the term of this patent is extended or adjusted under 35 U.S.C. 154(b) by 1102 days.

(21) Appl. No.: 11/398,829

(22) Filed: Apr. 5, 2006

(51) Int. Cl.
*A61L 9/00* (2006.01)
*A62B 7/08* (2006.01)
*F23D 3/28* (2006.01)
*F23Q 2/08* (2006.01)
*F23D 3/16* (2006.01)
*A01M 13/00* (2006.01)
*A01M 1/20* (2006.01)
*F21L 19/00* (2006.01)

(52) U.S. Cl. .............. 422/306; 422/1; 422/5; 422/120; 422/125; 422/126; 422/305; 431/295; 431/296; 431/297; 431/298; 431/327; 431/18; 431/120; 431/129; 431/144; 431/343; 431/344; 431/345; 431/350; 431/354; 431/356; 43/1; 43/124; 43/125; 43/144; 362/161; 362/392; 362/810

(58) Field of Classification Search .............. 422/1, 422/5, 120, 125, 126, 305, 306; 431/295–298, 431/327, 18, 120, 129, 144, 343–345, 350, 431/354, 356; 43/1, 124–125, 144; 362/161, 362/392, 810
See application file for complete search history.

(56) References Cited

U.S. PATENT DOCUMENTS 550,961 A * 12/1895 Galtier ................... 431/88
4,281,672 A * 8/1981 Caraway ................ 131/174

* cited by examiner

*Primary Examiner*—Jill Warden
*Assistant Examiner*—Monzer R Chorbaji
(74) *Attorney, Agent, or Firm*—Risto A. Rinne, Jr.

(57) ABSTRACT

An apparatus for controlling a duration of burn of a stick of incense includes a base and a ferric rod extending away from and over the base. A hole is provided in the base for placement of a bottom end of the incense. A cylindrical portion is adapted to fit over and slide along a longitudinal length of the incense. A magnet is attached to the cylindrical portion and is adapted to secure the cylindrical portion, where desired, along a longitudinal length of the rod. Accordingly, the incense is supported in two locations and is disposed under and generally parallel to the rod. The incense is able to burn until the area of combustion reaches the cylindrical portion, at which time it is extinguished. Two alternate embodiments are described that allow use of modified forms of the cylindrical portion with prior art types of incense burners.

11 Claims, 4 Drawing Sheets

INCENSE TIMER

BACKGROUND OF THE INVENTION

1. Field of the Invention

The present invention, in general relates to burning incense sticks and, more particularly, to a timer for controlling the duration of burn.

Incense sticks are well-known devices that are used in religious ceremonies, general gatherings, and for private use to imbue an area with a particular scent via smoke.

The incense stick is typically placed in a holder that cooperates with a bottom end of the incense stick. The top of the incense stick is then ignited by a match or other type of lighter.

If a flame appears, it is extinguished and a dull red glow remains at the tip of the incense stick to continue the combustion process. As combustion of the stick occurs, a thin stream of smoke rises from the incense stick to mingle with and disappear from view into the ambient air.

An incense stick burns itself by smoldering at the tip. A residue of ash remains as the tip continues to smolder in what is usually a generally downward direction toward a base of the incense stick. When the ash residue becomes sufficiently large, it falls from the incense stick.

It is both the combustion process and the smoke that impart the greatest concentration of odor into the environment. While the incense stick, if held to one's nose, may have an odor of its own, it is the combustion process that maximally emits the fragrance of that particular type of incense stick.

Different types of incense sticks have a different odor. While they do vary somewhat in size, incense sticks tend to be similarly sized.

When a person enters an area (i.e., a room) where incense has been burning for a short period of time, the person is likely to notice a pleasant scent to the air. It is for this reason, primarily, that people burn incense sticks.

There are other reasons for burning incense, to be sure. For example, it is not uncommon for a person to place a burning stick of incense on an altar or in front of an image of a holy being or saint as an offering in veneration that accords with their spiritual practices.

While the burning of incense sticks affords certain benefits, their use is also problematical. When an incense stick is ignited it tends to burn from a tip toward a base until all of a combustible coating that also contains the primary fragrance, has been consumed.

Accordingly, there is no effective way to regulate the duration of burn of an incense stick.

When all of an incense stick is burned in a confined space or where there is little movement of air, the fragrance can overpower the area. When that happens, the scent becomes overbearing and instead of adding to the ambiance of the area, can actually detract from the ambiance.

Therefore, a person may want to burn only a portion of a stick of incense. The person may want to burn the stick for, perhaps, twenty minutes at a time in order to provide the perfect olfactory room aesthetics.

Also, when prayers or supplications are complete, the person may want to terminate the burning of incense as a natural conclusion of the ritual itself.

To extinguish a burning (i.e., smoldering) stick of incense, the person may try to do so by grasping a burning tip of the incense stick and pinching the tip between a thumb and a finger. However, this action can easily burn the person.

Also, if it is not done sufficiently well, the incense stick can appear to be extinguished while a small portion of the tip still smolders faintly. The faintly smoldering tip may not emit enough smoke to be visible or have any visible glow. Accordingly, the person believes the incense stick is extinguished.

A few minutes later, the entire tip can begin to fully smolder unbeknownst to the person who thought he or she had extinguished it. Eventually, the entire incense stick will burn itself out and a far too strong of a fragrance will permeate the area.

There is also a fire danger associated with incense burning. Certain prior art types of incense stick holders do not well-secure the incense stick above the holder. Sometimes, when the ash residue falls from the incense stick, it brings a small smoldering ember along with it. If the smoldering ember falls on the holder it usually soon extinguishes itself and no harm is done.

By apparent reason of market demand, most incense holders are narrow devices that suspend the stick of incense at an angle over the holder. If a longitudinal axis of the incense stick does not align with a longitudinal axis of the holder, a portion of the incense stick can extend beyond the holder.

If the incense stick is offset off of the holder, the smoldering ember can fall on a combustible surface and ignite it. Clearly, this can cause considerable property damage and even death.

Additionally, it is preferred that all ash fall onto the holder so that the holder can later be held over a trash receptacle and tilted to deposit all of the ash into the receptacle and maintain the general area of the holder as clean as possible.

A person who has just completed a stay in an area that includes a burning stick of incense will want to extinguish that stick so as to prevent a risk of fire prior to leaving.

If, as mentioned above, the person pinches the incense stick, believes it to be extinguished, and then leaves the area, there remains a possibility that a small smoldering remnant of the incense stick can bring it back into full smolder. If the stick is also offset off of the holder, there remains the possibility that a fire could occur as a result of falling ash and ember.

Another prior way of extinguishing a stick of incense is to remove the burning stick from its holder and dip the tip into a glass of water. While this is effective at extinguishing the incense stick, it also damages the remainder of the stick.

When the person tries to reignite the tip, it may no longer combust. This wastes incense sticks. Many people presently accept this waste as a necessary financial burden.

If an incense stick if capable of burning for several hours duration, the person may burn it for only a few minutes and then extinguish it by dipping it in water. The person may then discard the remainder, which is substantially unused, and use a new incense stick for the next few minute duration burn.

If the person extinguishes by dipping (i.e., soaking) the incense stick in water, and then decides a few minutes after extinguishing it that he or she would like to continue to burn it for an additional period of time, it is virtually impossible to reignite a soaked incense stick.

The person will be forced to use a new stick and will likely discard the prior stick of incense, even though the greater portion of it was unused.

Accordingly, there exists today a need for an incense timer that helps ameliorate the above-mentioned problems and difficulties.

Clearly, such an apparatus would be a useful and desirable device.

2. Description of Prior Art

Incense holders are, in general, known. For example, the following patent describes a somewhat related type of device:

U.S. Pat. No. 6,389,739 to Borut, et al., that issued on May 21, 2002.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide an incense timer that is useful to control the duration of burn of a stick of incense.

It is also an important object of the invention to provide an incense timer that will extinguish a stick of incense after a period of time.

Another object of the invention is to provide an incense timer that will extinguish a stick of incense but will not damage the stick of incense.

Still another object of the invention is to provide an incense timer that will automatically extinguish a stick of incense after a period of time and permit continued use of a remainder of the stick of incense.

Still yet another object of the invention is to provide an incense timer that includes means for regulating the duration of burn of a stick of incense.

Yet another important object of the invention is to provide an incense timer that includes means for regulating the duration of burn of a stick of incense that can be quickly adjusted.

Still yet another important object of the invention is to provide an incense timer that provides a holder for supporting a stick of incense for combustion.

A first continuing object of the invention is to provide an incense timer that provides a holder for supporting a stick of incense for combustion and wherein the holder retains the stick in a preferred position over the holder.

A second continuing object of the invention is to provide an incense timer that is adapted for use with existing types of incense stick holders.

A third continuing object of the invention is to provide an incense timer that is adapted for use with existing types of incense stick holders by attaching the incense timer to the existing incense stick holder.

A fourth continuing object of the invention is to provide an incense timer that is adapted for use with existing types of incense stick holders by attaching the incense timer to the incense stick.

A fifth continuing object of the invention is to provide an incense timer that helps to ensure that all of the ash that is produced as a result of burning a stick of incense falls on a portion of the incense timer.

A sixth continuing object of the invention is to provide an incense timer that helps to ensure that all of the ash that is produced as a result of burning a stick of incense falls on a base of the incense timer.

A seventh continuing object of the invention is to provide an incense timer that makes it easier and faster to install a stick of incense in the device than with prior art devices.

An eighth continuing object of the invention is to provide an incense timer that provides a safe incense burner.

A ninth continuing object of the invention is to provide an incense timer that provides a safe incense burner and which controls a duration of burn of a stick of incense.

Briefly, an incense timer that is constructed in accordance with the principles of the present invention has a base that is adapted to receive a lower portion of a stick of incense. A member is attached at one end thereof to the base and extends upward at an angle over a remaining portion of the base. A cylindrical portion that is adapted to fit over the stick of incense and slide along a longitudinal length of the stick of incense is placed over the stick of incense and is secured to the member along a longitudinal length of the member. The stick of incense will combust (i.e., smolder or burn) until a smoldering portion reaches the cylindrical portion. The free flow of air around the stick of incense is then sufficiently impeded so as to reliably extinguish the stick of incense at the beginning of the cylindrical portion. A preferred method for securing the cylindrical portion to the member is described. According to a first modification, a first modified cylindrical portion is attached to a first end of a flexible member. An opposite end of the flexible member includes means for attaching the flexible member to a prior art existing type of an incense holder. The incense stick is urged in the first modified cylindrical portion where it is held in position and is able to burn until the smoldering portion reaches the modified cylindrical portion. According to a second modification, a second modified cylindrical portion that includes means therein sufficient to retain the second modified cylindrical portion along a preferred longitudinal length of the stick of incense is urged over the stick of incense to the desired position. The stick of incense with the second modified cylindrical portion are placed in a prior art existing type of incense stick holder and the stick of incense is burned until a smoldering portion thereof reaches the second modified cylindrical portion, at which time the stick of incense is extinguished. Accordingly to any embodiment of the instant invention, a remaining portion of the stick of incense can be reignited and burned. The process can be repeated, as desired, to precisely control a duration of burn. Additionally, the first embodiment ensures that the stick of incense will be disposed over the base, thereby virtually eliminating the possibility that any ash or burning embers from the stick of incense can fall onto a surface other than the base.

DETAILED DESCRIPTION OF THE INVENTION

Figure 1:
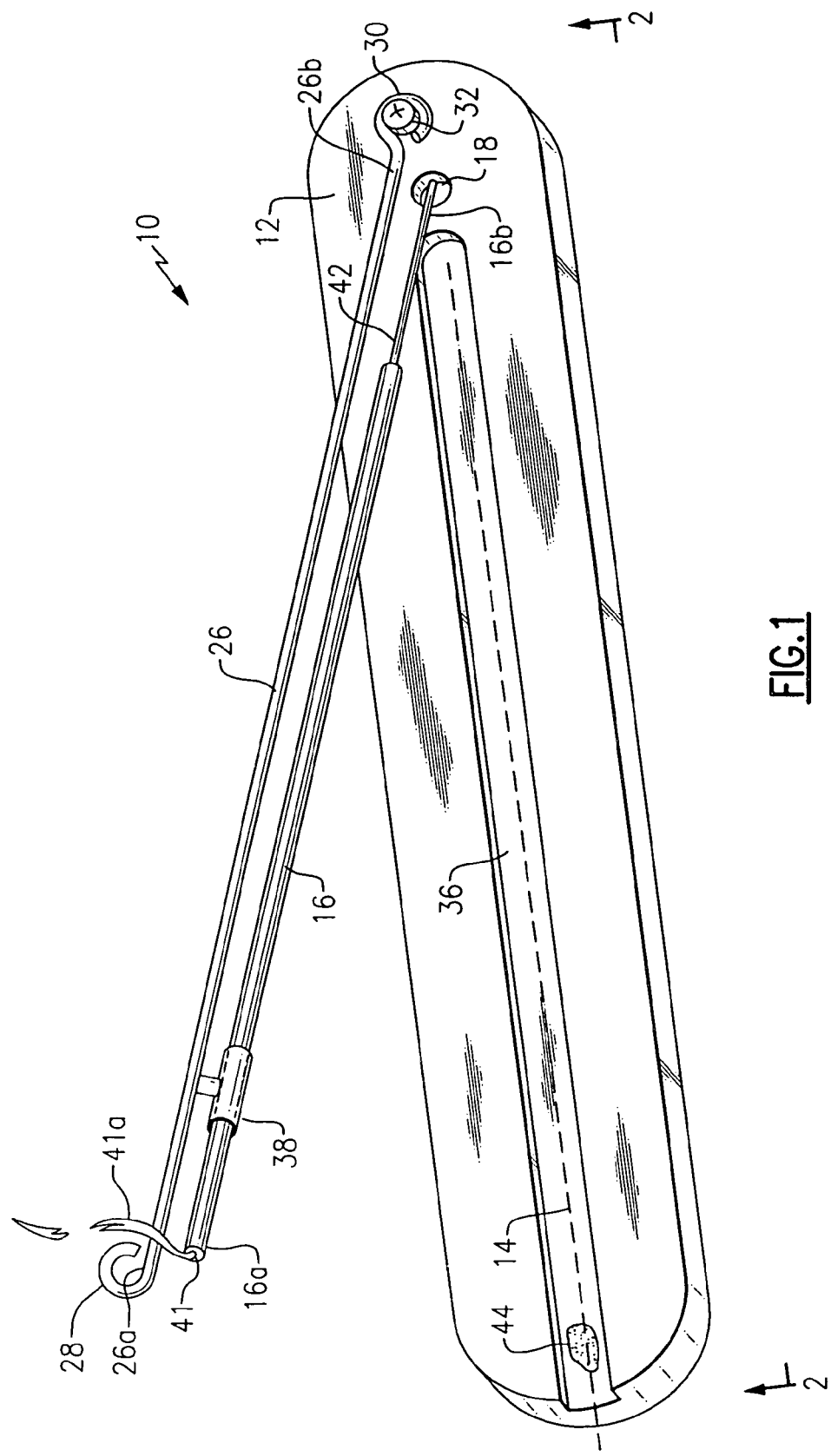
FIG. 1 is view in perspective of an incense timer.
Figure 2:
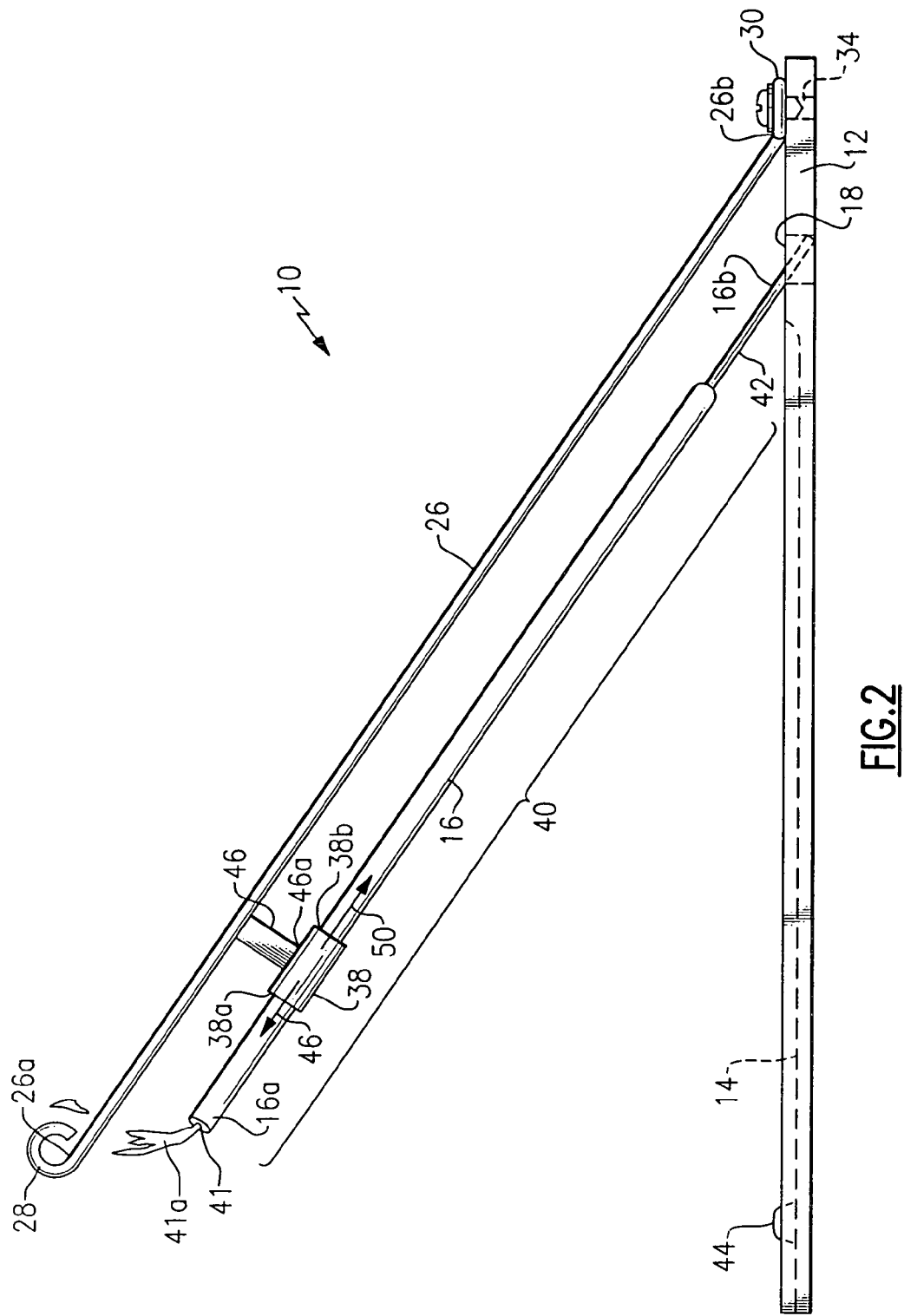
FIG. 2 is a side view of the incense timer of FIG. 1 taken along the line 2-2 of FIG. 1.

Referring to all of the drawing figures and now, primarily to both FIG. 1 and FIG. 2 is shown, an incense timer, identified in general by the reference numeral 10.

The incense timer 10 includes a generally planar base 12 that preferably includes an ash slot 14 that extends along a longitudinal length of the base 12. The base 12 is made of any preferred material, including wood, plastic, or any other preferred sufficiently fire-resistant material.

A burning stick of incense 16 is disposed at an angle with respect to the base 12. The incense 16 includes an upper end 16a and a bottom end 16b.

The incense timer 10 functions as a sophisticated type of an incense 16 holder for the stick of incense 16 that also controls a duration of burn time for the stick of incense 16 in a precise and predicable way that can be readily observed, and therefore set, accordingly. This is described in greater detail hereinafter.

The base 12 includes a hole 18 or recess into which the bottom end 16b of the incense 16 is inserted.

An advantage of the design of the incense timer 10 is that the hole 18 can be drilled (or formed) so as to be considerably larger than an outside diameter of the bottom end 16b of the stick of incense 16.

With a prior art type of incense burner (See reference numeral 20, FIG. 4) a small diameter clearance hole 22 is provided in an upraised portion 24 of the prior art type of incense burner 20. In order to retain the stick of incense 16 at the desired angle relative to the prior art type of incense burner 20, a small diameter clearance hole 22 that is only slightly larger than the outside diameter of bottom end 16b of the stick of incense 16 is required.

The prior art type of incense burner 20 also requires that the clearance hole 22 include a longitudinal axis that aligns with a longitudinal axis of the stick of incense 16, when the incense 16 is placed therein.

The small clearance hole 22 and critical alignment between the two axes combine to make it especially difficult to insert or to remove the bottom end 16b into or from the clearance hole 22 of the prior art type of incense burner 20 as the bottom end 16b must be carefully aligned with and then urged, perhaps even forced, to enter sufficiently far into the clearance hole 22.

The large diameter hole 18 also permits rapid insertion (or removal) of the stick of incense 16 into (or from) the hole 18, as is described in greater detail hereinafter.

Also, the hole 18 can be drilled at a right angle (or virtually at any other angle) with respect to the base 12, even though the stick of incense 16 will not be disposed at a right angle (or the angle drilled). This allows for easy, non-critical drilling of the hole 18.

A rod 26 includes an upper end 26a and an opposite lower end 26b. The rod 26 includes a longitudinal axis that is disposed at substantially the same angle as that which the longitudinal axis of the stick of incense 16 is disposed with respect to the base 12.

The rod 26 can be formed of any desired material. A preferred material includes a steel or other ferric material that is curved in a first loop 28 at the upper end 26a and in a second loop 30 at the lower end 26b. An advantage of the rod 26 being formed of a ferric material (i.e., steel) is described in greater detail, hereinafter.

The plane of the first loop 28 is generally perpendicular with the plane of the second loop 30. The plane of the second loop 30 is parallel with a plane of the base 12. The plane of the first loop 28 is parallel with the longitudinal axis of the rod 26.

The first and second loops 28, 30 eliminate sharp ends at the upper end 26a and at the lower end 26b of the rod 26, thereby helping to prevent injury, for example, a puncture wound from possibly occurring.

It is preferred that the incense timer 10 be shipped in a disassembled state to minimize the volume required to house it. A recipient secures the rod 26 to the base 12 by a first passing a screw 32 though the second loop 30 and into a predrilled screw hole 34 that is provided in the base 12.

The screw 32 is tightened while maintaining the longitudinal axis of the rod 26 parallel with and above a center longitudinal axis 36 (dashed line) of the base 12. This secures the rod 26 in the desired position, as shown in FIG. 1 and in FIG. 2.

A cylindrical portion 38 is included that includes an inside diameter that is greater than the outside diameter of the stick of incense 16 where a coating is located, the coating being identified in general by bracket 40. The coating 40 is a material that is included along the longitudinal length of the stick of incense 16 to aid combustion and provide the desired odor.

The coating 40 is burned during use. In actual use, any flame that may initially occur is extinguished by the user, leaving behind a reddish glowing ember 41. Therefore, a portion of the stick of incense 16 proximate the glowing ember 41 continues to smolder at a slow rate. When the terms "burn", "burned", or "consumed" are used herein, it is the smoldering action of the glowing ember 41 that is being referred to.

A column of smoke 41a rises upward from the glowing ember 41 because it is warmer than the surrounding ambient air.

The coating 40 is applied longitudinally over a center member 42 of the stick of incense 16. The center member 42 is typically formed of a slender piece of wood.

Both the coating 40 and the center member 42 of the incense 16 are consumed from the upper end 16a toward the bottom end 16b as the stick of incense 16 is progressively burned. Ash 44 is a by-product of combustion that eventually falls onto the base 12 and into the ash slot 14, if one is provided.

When the last of the coating 40 has been consumed, the remainder of the center member 42 is generally not able to continue to smolder without the aid to combustion that was provided by the coating 40. Accordingly, a small portion of the center member 42 remains after the stick of incense 16 has been fully consumed.

The cylindrical portion 38 is able to slide up or down along the longitudinal length of the stick of incense 16, as desired. The cylindrical portion 38 includes an upper end 38a and an opposite lower end 38b.

A magnet 46 is attached at a first magnet end 46a to the cylindrical portion 38. Attachment of the magnet 46 to the cylindrical portion 38 may be by adhesion (i.e., epoxy, etc.), magnetic attraction, or by any preferred method.

If the rod 26 is formed of steel (ferric) the magnet 46 will adhere anywhere along the longitudinal length of the rod 26 where it is placed. In use, the magnet 46 and the cylindrical portion 38 are simultaneously urged (i.e., slid) along the longitudinal length of the rod 26, either up in a direction as shown by arrow 48 or down in a direction as shown by arrow 50 into the desired position, and then released.

The magnet 46 then secures itself and the cylindrical portion 38 in position, relative to the rod 26. The cylindrical portion 38 retains a portion of the stick of incense 16 therein and, accordingly, provides the unexpected benefit of also supporting a portion of the weight of the stick of incense 16.

Furthermore, as a portion of the weight of the stick of incense 16 is supported by the cylindrical portion 38, the stick of incense 16 is secured at a second location that is disposed away from the lower end 16b. Therefore, the incense timer 10 provides an unexpected benefit of supporting the stick of incense 16 simultaneously at two locations.

Accordingly, the stick of incense 16 is prevented from being displaced either to the left or to the right of the center longitudinal axis 36 of the base 12.

This provides a substantial unexpected benefit of ensuring that the ash 44 must fall onto the base 12 and into the ash slot 14 (if provided). This is significant because there is always a possibility that the ash 44, when it falls from the upper end 16a of the stick of incense 16, can include a small amount of the glowing ember 41.

If the ash 44 along with a portion of the glowing ember 41 were to fall off of the base 12 (as is likely with the prior art type of incense burner 20 that cannot positively retain the incense 16 over the prior art incense burner 20), the ash 44 and ember 41 could land on a highly combustible surface, for example on a nearby piece of paper, and start a catastrophic fire.

The magnet 46 and the cylindrical portion 38, both being secured to the rod 26, retain the incense 16 and prevent the ash 44 from landing off of the incense timer 10.

Of course, if the incense timer 10 were used in gale force winds anything could happen, however, the incense timer 10 is expected to be used indoors and with only a slight amount of air motion. Accordingly, when used as intended the incense timer 10 is safer than the prior art types of incense burners 20.

Of course, there are other ways of attaching the cylindrical portion 38 to the rod 26 which permit placement of the cylindrical portion 38 where desired along the longitudinal length of the rod 26.

For example, a clip (not shown) could be attached to the cylindrical portion 38 and secured where desired along the longitudinal length of the rod 26.

Alternately, a smaller cylinder (not shown) could be disposed over the rod 26 and also attached to the cylindrical portion 38. If the smaller cylinder included a sufficiently tight fit (i.e., a friction-fit) with respect to the rod 26, the smaller cylinder along with the cylindrical portion 38 could both be simultaneously urged (i.e., slid) in the direction of arrows 48 or 50 and would retain its position when released.

It is important to allow the cylindrical portion 38 to be displaced up or down, in the direction of arrows 48 and 50, as desired over the stick of incense 16.

This is because while the stick of incense 16 is burning the location of the glowing ember 41 moves slowly and steadily toward the upper end 38a of the cylindrical portion 38 as the stick of incense 16 is progressively consumed. Prior to the glowing ember 41 reaching the upper end 38a of the cylindrical portion 38, ambient air is able to flow freely around the stick of incense 16 proximate the glowing ember 41.

However, as soon as the glowing ember 41 reaches the upper end 38a of the cylindrical portion 38, the free flow of ambient air around the glowing ember 41 is impeded. As a result the glowing ember 41 is automatically and predictably extinguished as soon as it reaches the upper end 38a and begins to enter into the cylindrical portion 38.

A user can then determine (or the manufacture of the stick of incense 16 can provide this information) as to what rate the stick of incense 16 is normally consumed. Not as any intended limitation but only to illustrate some of the substantial benefit that the incense timer 10 provides, assume that the stick of incense 16 is consumed (burned) at an average rate of one inch consumed per every fifteen minutes burn duration, when the incense 16 is disposed at a normal attitude, as shown.

If the user wants a total fifteen minute burn time because he or she expects that the ceremony, prayer, event, or other activity will be concluded in that amount of time, or if it is deemed that a fifteen minute burn duration will emit a proper, ideal amount of fragrance (odor) by the incense 16 into the area, the user would then urge the cylindrical portion 38 along the length of the incense 16 until the upper end 38a of the cylindrical portion 38 was disposed initially about one inch down from the upper end 16a thereof in the direction of arrow 50.

The user would then ensure that the magnet 46 is disposed against the rod 26 sufficient to retain the cylindrical portion 38 in the position it was set to. The user would then ignite the incense 16 and basically forget about it. When about fifteen minutes of time has elapsed the glowing ember 41 will reach the upper end 38a and be automatically extinguished.

Another benefit is that no damage occurs to the stick of incense 16. If it is deemed that another fifteen minutes (or any other amount of time) of burn duration is required, the user simply urges the cylindrical portion 38 another inch in the direction of arrow 50 and reignites the glowing ember 41 at the remaining (new) upper end 16a. This process is repeated to provide the ultimate in ease and predictability of regulating a duration of burn time for the stick of incense 16.

Another unexpected benefit is also provided. If, for example, the initial burn time was set to thirty minutes, that is the upper end 38a of the cylindrical portion 38 was initially displaced two inches (according to the example used herein) down from the upper end 16a, and it is deemed that a sufficient amount of odor has been emitted into the area, the user simply slides (urges) the cylindrical portion 38 in the direction of arrow 48 until the upper end 38a reaches the glowing ember 41.

The glowing ember 41 (and the incense 16) will then be soon extinguished.

If the cylindrical portion 38 is urged somewhat too far in the direction of arrow 48 so that the glowing ember 41 is disposed inside a longitudinal length of the cylindrical portion 38, the flow of ambient air around the glowing ember 41 will still be disrupted sufficient to extinguish the glowing ember 41. The incense timer 10 provides a highly reliable way to regulate burn duration of the incense 16.

Obviously, it will be apparent to the user if he or she urges the cylindrical portion 38 so far in the direction of arrow 48 as to go beyond the remaining upper end 16a.

The dimensions of the cylindrical portion 38 are not critical. A preferred length is about one-half of an inch although the length can be varied as can the material it is made from.

To use the incense timer 10, the rod 26 is attached as was described above. The magnet 46 is applied to the rod 26 somewhere along the length of the rod 26 with the cylindrical portion 38 disposed under the rod 26. The lower end 16b of the incense 16 is urged into the upper end 38a of the cylindrical portion 38, through the cylindrical portion 38, toward the base 12, and into the hole 18 provided in the base 12.

The cylindrical portion 38 is then urged in either the direction of arrow 48 or arrow 50 to provide the desired duration of burn for the incense 16, which is then ignited, consumed, and extinguished at the predetermined, desired time.

To continue use of the incense 16, the cylindrical portion 38 is urged a desired amount in the direction of arrow 50 and released. It is again retained in position by cooperation of the magnet 46 with the rod 26. The newly exposed upper end 16a of the stick of incense 16 is again ignited and the process is repeated until the entire stick of incense 16 has been consumed.

When the final portion of the incense 16 is to be consumed the user urges the upper end 38a of the cylindrical portion 38 down in the direction of arrow 48 beyond the bottom of the coating 40. The incense 16 then burns until the coating 40 is consumed and then it naturally extinguishes itself.

While the incense timer 10 provides a superior type of incense 16 burner, there are many of the prior art types of incense burners 20 currently in use. Some have sentimental or other value and therefore certain users may wish to continue to use their prior art types of incense burners 20 while still take advantage of the benefits of the incense timer 10, as disclosed herein.

Figure 3:
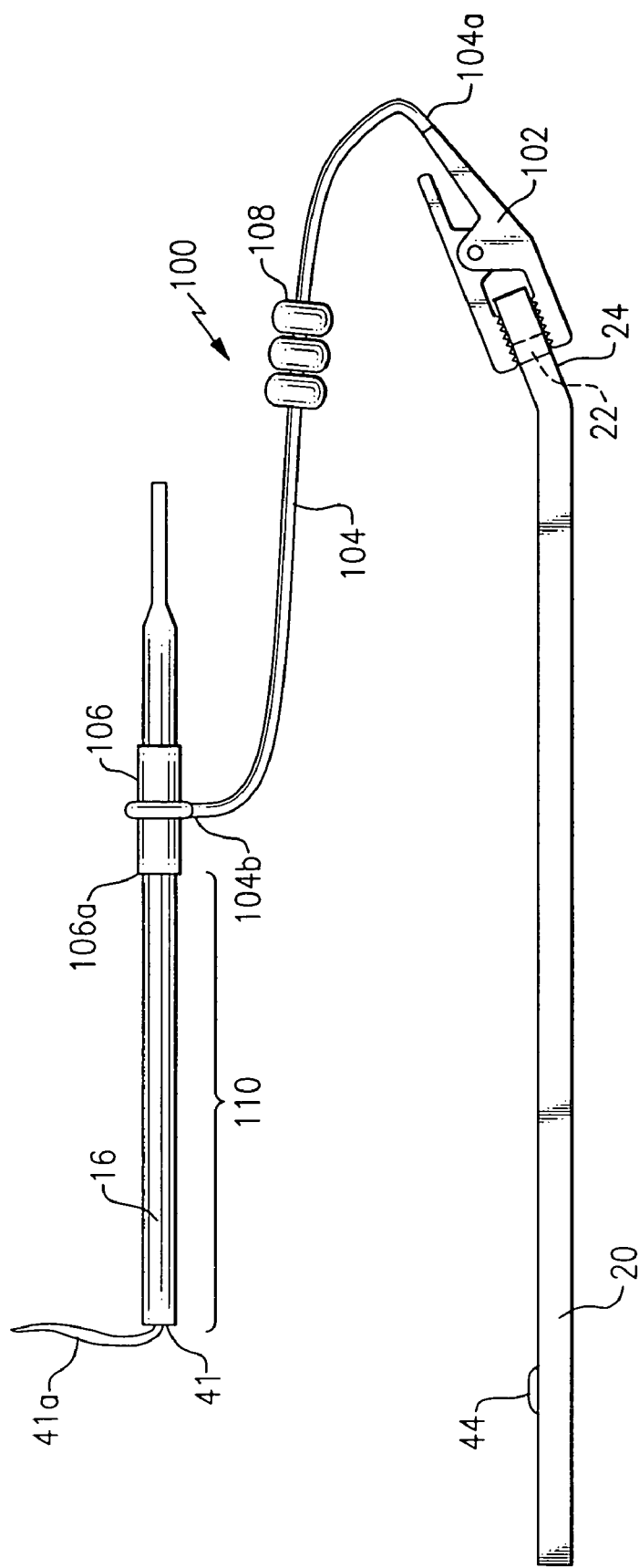
FIG. 3 is a side view of a first modified type of an incense timer used with an existing type of an incense stick holder.
Figure 4:
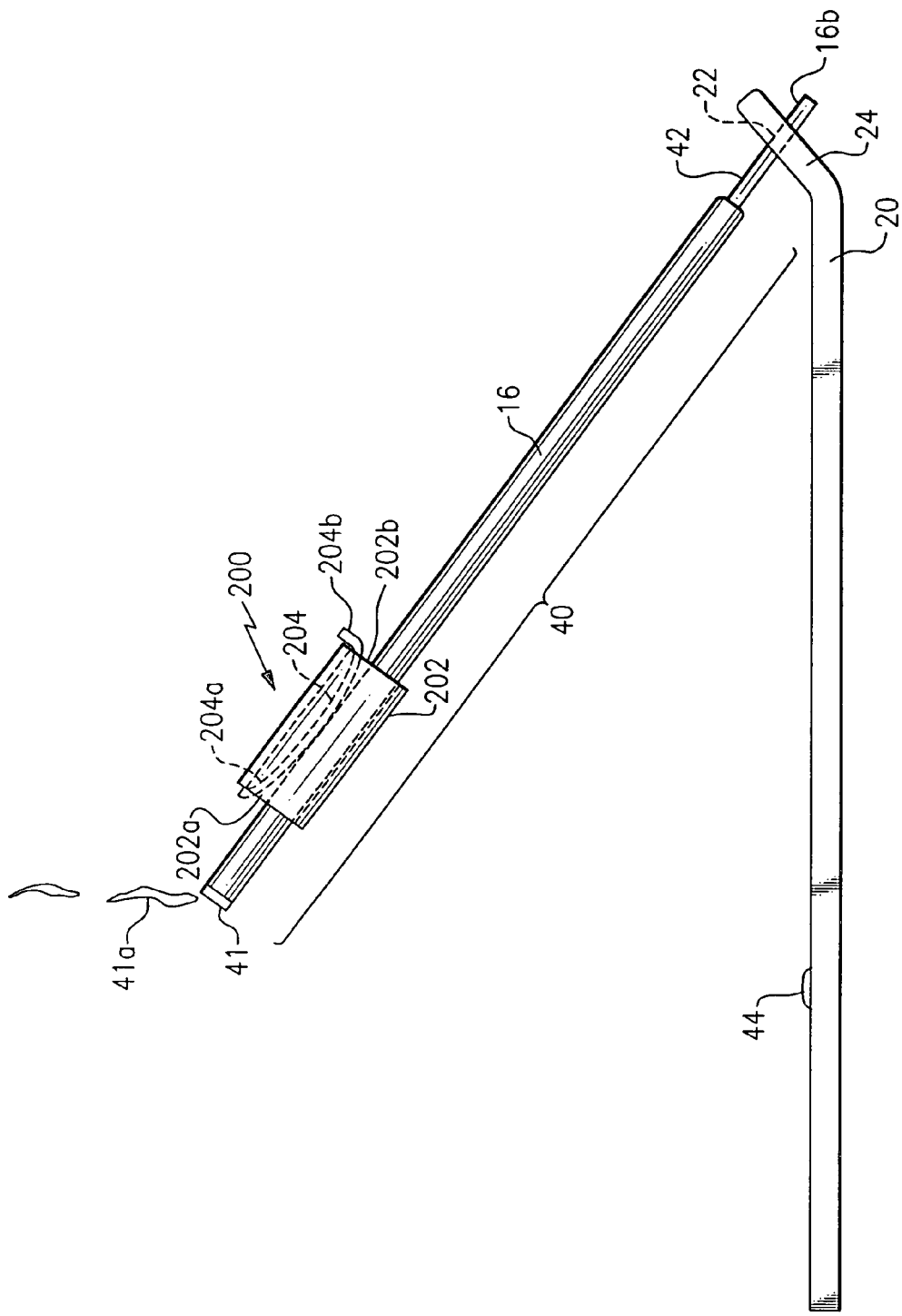
FIG. 4 is a side view of a second modified type of an incense timer used with an existing type of an incense stick holder.

For such use, a first modified type of an incense timer 100 that is used with the existing prior art type of an incense holder 20 is shown in FIG. 3 and a second modified type of an incense timer 200 that is used with the existing prior art type of an incense holder 20 is shown in FIG. 4.

Referring now primarily to FIG. 3, the first modified type of an incense timer 100 includes a clip 102 for attachment to the upraised portion 24 of the prior art type of incense holder 20.

A flexible member 104 is attached at a first end 104a thereof to the clip 102 and to a modified type of the cylindrical portion 106 at an opposite end 104b thereof.

The modified type of cylindrical portion 106 is identical to the cylindrical portion 38 of the incense timer 10, except the modified type of cylindrical portion 106 does not include the magnet 46 because it is not attached to the rod 26.

The flexible member 104 is malleable into position and when formed retains its position, as set. A solid copper wire, similar to that used in house wiring (for example, solid copper 12 or 14 gauge electrical wire) is suitable for use as the flexible member 104. Accordingly, the flexible member 104 can be soldered to both the clip 102 and the modified cylindrical portion 106, as desired. If desired, an ornamental coating 108, like beads, can be disposed along the longitudinal length of the flexible member 104.

In use, the flexible member 104 is urged to any preferred shape sufficient to dispose the modified cylindrical portion 106 in such a position wherein a longitudinal axis of the modified cylindrical portion 106 is elevated above and parallel with a longitudinal axis of the prior art type of incense burner 20.

The stick of incense 16 is placed, therein as shown with a first end 106a of the modified cylindrical portion 106 set a predetermined distance, as shown by bracket 110, away from the burning ember 41.

The distance of the bracket 110 in a preferred unit of measurement, multiplied by the rate of burn per unit of time, yields the time until the burning ember 41 reaches the first end 106a of the modified cylindrical portion 106 and is extinguished.

The first modified type of an incense timer 100 provides a method to regulate the time of burn for the incense 16 that can be used with the prior art type of the incense burner 20.

It also provides additional support to the stick of incense 16 which is held in alignment with the longitudinal axis of the modified cylindrical portion 106. For this to optimally occur, the inside diameter of the modified cylindrical portion 106, while having to be larger than the outside diameter of the coating 40, is preferably only slightly greater in order to prevent excessive shifting of the longitudinal axis of the incense 16 relative to the longitudinal axis of the modified cylindrical portion 106.

The longitudinal axis of the modified cylindrical portion 106 is set, as described above, to be parallel with the longitudinal axis of the prior art type of incense burner 20. This ensures that the ash 44 residue will fall onto the prior art type of the incense burner 20.

Referring now primarily to FIG. 4, the second modified type of an incense timer 200 includes a further modified cylindrical portion 202.

The further modified cylindrical portion 202 is similar to the cylindrical portion 38 and to the modified cylindrical portion 106 in that all three are adapted to be placed over the coating 40 and to slide (i.e., adapted to be displaced) along the longitudinal length of the stick of incense 16.

However, unlike the cylindrical portion 38 and the modified cylindrical portion 106, the further modified cylindrical portion 202 does not include any additional support structure.

Rather, the further modified cylindrical portion 202 includes means for retaining it at any position along the longitudinal length of the stick of incense 16 that it is urged to.

This means that the further modified cylindrical portion 202 can be used with the stick of incense 16 that is, itself, inserted and secured in a conventional way to the prior art type of incense burner 20.

Certain users may prefer this approach even though the second modified type of an incense timer 200 does not provide an additional support that helps maintain the longitudinal axis of the stick of incense 16 in alignment with the longitudinal axis of the prior art type of incense burner 20.

Accordingly, there is risk that the incense 16 could shift in its position and that the ash 44 residue might fall off of the prior art type of incense burner 20. Also, that portion of the center member 42 that does not include the coating 40 may be bent, as sometimes happens.

This can cause a portion of the stick of incense 16, even when the stick of incense 16 has been inserted properly into the prior art type of incense burner 20, to extend away from the prior art type of incense burner 20 so that the falling ash 44 residue may not land on the prior art type of incense burner 20. The drawing figure shows the ash 44 residue on the prior art type of incense burner 20.

A preferred method of securing the further modified cylindrical portion 202 where desired to the stick of incense 16 includes an inner member 204 (dashed lines) that is disposed in the further modified cylindrical portion 202 and makes contact with the coating 40 when the further modified cylindrical portion 202 is urged over the coating 40, as shown.

The inner member 204 acts as a weak leaf spring. It applies a force on the coating 40 which increases the static coefficient of friction between the further modified cylindrical portion 202 and the stick of incense 16 sufficient to retain the further modified cylindrical portion 202 in any position along the longitudinal length of the stick of incense 16 that also includes the coating 40.

The inner member 204 can be formed of any preferred material, including any preferred metal. The inner member 204 must be able to withstand the heat generated by the glowing ember 41 when it makes contact with an upper end 202a of the further modified cylindrical portion 202.

The inner member 204 includes an upper end 204a and an opposite lower end 204b. The upper end 204a of the inner member 204 is attached to the further modified cylindrical portion 202 at the upper end 202a thereof by soldering or by any other preferred method.

The inner member 204 includes an arcuate shape that extends toward an inside of the further modified cylindrical portion 202 as the inner member 204 extends longitudinally toward an opposite lower end 202b of the further modified cylindrical portion 202.

The inner member 204 is disposed closest toward the middle of the further modified cylindrical portion 202 at a center thereof, and then the arcuate shape of the inner member 204 directs it away from the middle of the further modified cylindrical portion 202 and back again toward an inside surface of the further modified cylindrical portion 202 at the lower end 202b thereof.

The lower end 204b of the inner member 204 extends slightly beyond the lower end 202b of the further modified cylindrical portion 202. The lower end 204b of the inner member 204 is not attached to the lower end 202b of the further modified cylindrical portion 202 so that it can be displaced longitudinally, as required, when the further modified cylindrical portion 202 is placed on the incense 16 and the inner member 204 is compressed by the coating 40.

Accordingly, the inner member 204 applies a force to the coating 40 sufficient to retain the further modified cylindrical portion 202 at any longitudinal location along a usable length (i.e., where the coating 40 is located) of the stick of incense 16.

In use, the further modified cylindrical portion 202 is urged along the length of the coating 40 to a desired position. As was generally described hereinabove for use of the incense timer 10 and the first modified type of an incense timer 100, the glowing ember 41 will similarly smolder until it reaches the upper end 202a of the second modified type of an incense timer 200. Then it will automatically extinguish itself.

Accordingly, a method for controlling the duration of burn of the stick of incense 16 is provided for use with the prior art type of incense burner 20 that permits normal insertion of the incense 16 into the prior art type of incense burner 20. Also, minimum visual impact occurs, thereby preserving the original aesthetics that are associated with use of the prior art type of incense burner 20.

Because the second modified type of an incense timer 200 does add weight to the stick of incense 16 without providing any additional support to secure the stick of incense 16 relative to the prior art type of incense burner 20, it is desirable that the combined weight of the further modified cylindrical portion 202 and the inner member 204 be kept as low as possible.

After having had benefit of the instant invention, further modification and the inclusion of other methods of securing the further modified cylindrical portion 202 along the longitudinal length of the stick of incense are possible.

For example, the inner member 204 could be replaced and a flame-retardant inner material, for example a ceramic weave similar to that used in woodstoves, could be adhered to the inside of the further modified cylindrical portion 202 to provide the necessary friction to secure it where desired along the length of the incense 16.

Similarly, any of the component parts of any embodiment of the invention (10, 100, 200) described herein may be modified to function optimally well with various sizes of the stick of incense 16.

If desired, the base 12 could be modified to simultaneously support a plurality of the incense sticks 16, if desired.

Similarly, the cylindrical portion 38, the modified cylindrical portion 106, and the further modified cylindrical portion 202 can be still further modified, as desired, to include a cross-sectional shape that is other than cylindrical (either on the inside, outside, or both aspects thereof), providing the modified non-cylindrical shape includes a sufficient inside dimension (i.e., diameter) to permit placement and longitudinal movement over the stick of incense 16.

If desired and according to another preferred possible modification, the lower end 26b of the rod 26 is welded, soldered, or otherwise attached to the base 12 during manufacture. Welding would eliminate the screw 32. If desired, the screw 32 could be installed and tightened by the manufacturer to spare the end-user of this task. According to this modification (whether the screw 32 is used or the lower end 26b is welded to the base 12), the rod 26 is initially disposed by the manufacturer so that it is parallel with respect to the base 12 for ease of shipment.

The user, upon receipt of the incense timer 10, would simply lift (i.e., urge) the upper end 26a of the rod 26 away from the base 12 until the rod 26 was disposed at a proper angle with respect to the base 12, typically about forty-five degrees. The rod 26 would then retain that position for future use. To complete preparation for use, the cylindrical portion 38 would then be attached by simply placing it against the rod 26 as shown in FIG. 1. This would eliminate any assembly by the user. If desired, the hole 18 could be attached to a separate member or block (not shown) that is, in turn, attached to the base 12.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. An incense timer, comprising:
   (a) a base;
   (b) means for positioning a stick of incense relative to said base;
   (c) means for controlling a duration of burn of said stick of incense, wherein said means for controlling a duration of burn includes means for extinguishing said stick of incense prior to a use of the entire stick of incense; and
   wherein said means for positioning said stick of incense relative to said base includes means for maintaining a portion of said stick of incense over said base, and wherein said means for maintaining a portion of said stick of incense over said base includes a rod attached to said base and extending therefrom, and wherein said rod is disposed over said base and includes means for securing said portion of said stick of incense to said rod.

2. The incense timer of claim 1 wherein said means for controlling a duration of burn of said stick of incense includes a cylindrical portion that includes an inside diameter that is larger than an outside diameter of said stick of incense, and wherein said cylindrical portion is adapted to be placed over said stick of incense and to be urged along a longitudinal length of said stick of incense.

3. The incense timer of claim 2 including means for maintaining said cylindrical portion at a predetermined position along said longitudinal length of said stick of incense.

4. The incense timer of claim 3 wherein said means for maintaining said cylindrical portion at a predetermined position includes means for securing said cylindrical portion to said means for positioning a stick of incense relative to said base.

5. The incense timer of claim 4 wherein said means for positioning a stick of incense relative to said base includes said means for maintaining a portion of said stick of incense over said base and wherein said means for maintaining a portion of said stick of incense over said base includes said rod attached to said base and extending therefrom, and wherein said rod is disposed over said base and including means for securing said cylindrical portion to said rod.

6. The incense timer of claim 5 wherein said means for securing said cylindrical portion to said rod includes a magnet attached to said cylindrical portion and wherein said rod includes a ferric material, and wherein said magnet is adapted to cooperate with said rod sufficient to retain said cylindrical portion along a longitudinal length of said rod.

7. The incense timer of claim 1 wherein said means for positioning a stick of incense relative to said base includes means for maintaining said stick of incense over said base.

8. The incense timer of claim 7 wherein said means for maintaining said stick of incense includes a flexible member that is sufficiently malleable to be bent into a desired position and which is capable of maintaining said desired position unless acted on by a further force, and wherein said flexible member includes means for securing said flexible member to said base and means for securing said stick of incense to said flexible member.

9. The incense timer of claim 8 wherein said means for securing said flexible member includes a clip attached to an end of said flexible member, said clip adapted to engage with said base.

10. The incense timer of claim 8 wherein said means for securing said stick of incense to said flexible member includes a modified cylindrical member that is attached to said flexible member and wherein said cylindrical member includes an inside diameter that is larger than an outside diameter of said stick of incense.

11. An incense timer, comprising:
 (a) a base;
 (b) means for positioning a stick of incense relative to said base;
 (c) means for controlling a duration of burn of said stick of incense, wherein said means for controlling a duration of burn includes means for extinguishing said stick of incense prior to a use of the entire stick of incense;
 (d) wherein said means for controlling a duration of burn of said stick of incense includes a cylindrical portion that includes an inside diameter that is larger than an outside diameter of said stick of incense, and wherein said cylindrical portion is adapted to be placed over said stick of incense and to be urged along a longitudinal length of said stick of incense;
 (e) including means for maintaining said cylindrical portion at a predetermined position along said longitudinal length of said stick of incense;
 (f) wherein said means for maintaining said cylindrical portion at a predetermined position includes means for securing said cylindrical portion to said means for positioning a stick of incense relative to said base; and
 (g) wherein said means for positioning a stick of incense relative to said base includes means for maintaining a portion of said stick of incense over said base and wherein said means for maintaining a portion of said stick of incense over said base includes a rod attached to said base and extending therefrom, and wherein said rod is disposed over said base and including means for securing said cylindrical portion to said rod.

* * * * *